United States Patent [19]

Smith

[11] Patent Number: 4,824,066
[45] Date of Patent: Apr. 25, 1989

[54] APPARATUS FOR AIDING IN THE STORING AND PRESERVING OF DONOR CORNEAS

[76] Inventor: S. Gregory Smith, Cloud Farm, Nine Gates Rd., Yorklyn, Del. 19736

[21] Appl. No.: 203,565

[22] Filed: May 25, 1988

Related U.S. Application Data

[63] Continuation of Ser. No. 483,636, Apr. 11, 1983, abandoned.

[51] Int. Cl.⁴ ............................................. A61B 19/00
[52] U.S. Cl. ..................... 248/500; 128/346; 269/243; 269/221; 269/287; 24/514
[58] Field of Search ................ 248/309.1, 187, 500, 248/507, 154; 128/305, 305.1, 310, 346; 206/5.1; 269/243, 221, 287; 356/246, 244; 220/325, 327, 89 A; 285/364, 328, 334.4; 134/137; 24/525, 569, 514

[56] References Cited

U.S. PATENT DOCUMENTS

| 2,881,500 | 4/1959 | Furness | 128/346 |
| 3,892,242 | 7/1975 | Honjyo | 128/346 |

FOREIGN PATENT DOCUMENTS

245988 11/1969 U.S.S.R. .

Primary Examiner—J. Franklin Foss
Assistant Examiner—Robert A. Olson
Attorney, Agent, or Firm—Peterson, Wicks, Nemer & Komrath

[57] ABSTRACT

An apparatus includes a lower ring member having a frusto-conical upper surface over which the sclera of the cornea to be transplanted is placed. An upper ring member is also included. Both ring members have registrable openings of a size such that only an annular portion of the sclera outwardly of the cornea is clamped when wing nuts are tightened on a number of threaded studs pivotally attached to the lower ring member. In this way enough clamping pressure can be exerted on the sclera to prevent flow of fluid therethrough into the corneal stroma.

10 Claims, 1 Drawing Sheet

U.S. Patent / Apr. 25, 1989 / 4,824,066
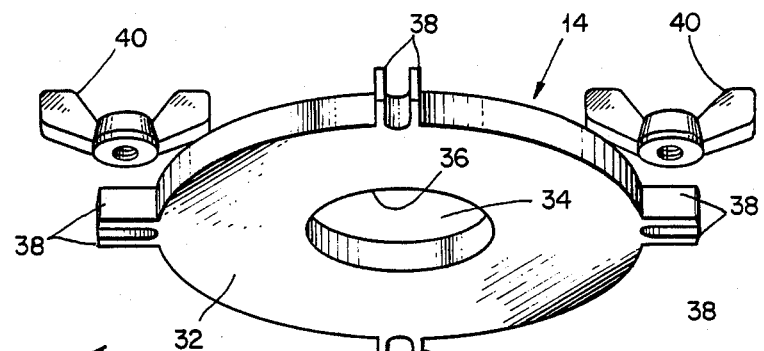
Fig 1
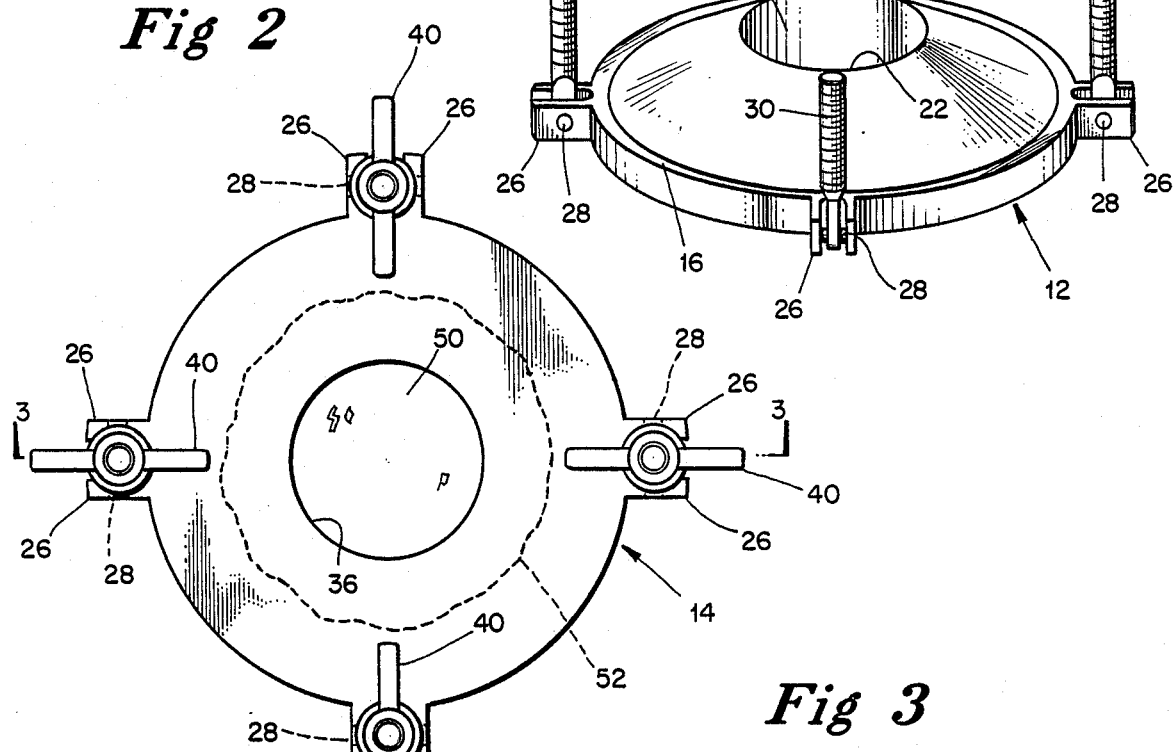
Fig 2
Fig 3
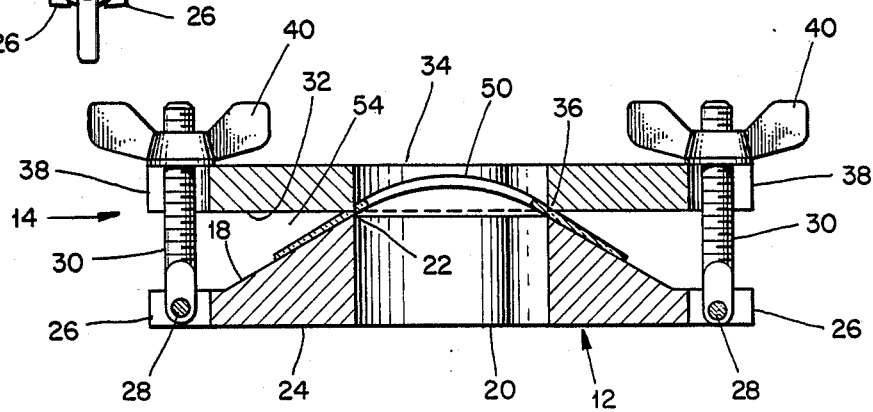

APPARATUS FOR AIDING IN THE STORING AND PRESERVING OF DONOR CORNEAS

This is a continuation of co-pending application Ser. No. 483,636 filed on Apr. 11, 1983.

BACKGROUND OF THE INVENTION

1. Field of the Invention

This invention relates generally to apparatus for aiding in the storing and preserving of donor corneas, and pertains more particularly to improved apparatus for optimumly clamping the sclera in a manner such that the cornea will not be damaged, either by the flow of fluid through the sclera into the corneal stroma or by any physical contact with the delicate endothelium overlying the posterior surface of the cornea.

2. Description of the Prior Art

Inasmuch as corneal transplants are now quite common, the need to preserve corneas from the time they are made available to the time that the transplant takes place has become of prime importance. To preserve the cornea, an organ culture media is made use of, such a media constituting a fluid with certain nutrients, trace metals and antibiotics included therein which will assist in the preservation of the cornea inasmuch as the cornea cells should be sufficiently nourished in order to assure their survival outside of the human body.

One device intended for use in helping to maintain a cornea in condition for subsequent transplanting is described in U.S. Pat. No. 2,929,603, granted on Mar. 22, 1960 to Gene A. Stewart for "CORNEAL CLAMP". The clamp described in said patent utilizes an underlying mounting plate on which a substantially hemispherical form is placed over which the cornea is positioned. The clamp includes in addition to the lower or mounting plate a second or upper plate having an opening therein of a size such that the cornea projects upwardly with respect thereto. The outer periphery of the upper plate is twistably engageable with the mounting plate.

Inasmuch as the underside of the cornea, this being the posterior side that has thereon the endothelium, is extremely sensitive to touch and contact with virtually any object causes it to die immediately. Consequently, any underlying form beneath the endothelium should be avoided. Furthermore, if the clamping pressure is not uniform with respect to the sclera surrounding the cornea, the endothelium continually pumps fluid out of the corneal stroma in an effort to keep the cornea thin but if the sclera is not compressed sufficiently, the fluid simply goes back into the corneal stroma through the relatively porous sclera. Stated somewhat differently, without uniform and complete compression of the sclera, the corneal stroma becomes thicker, and is therefore difficult to assess as far as its viability as a transplant, as well as becoming more difficult to surgically transplant. The undesired physical contact with the endothelium and the fluid flow through the sclera constitute two shortcomings of the clamp described in said Stewart patent.

Virtually the same inadequacies are present in the corneal transplant holder described in Russian Pat. No. 245,988 issued on Nov. 11, 1969. In this instance, transparent hemispherical elements or forms are utilized having flanges which are made of magnetized metal so that the hemispheres or forms can be held together by magnetic attraction. Not only is a surface involved that can adversely affect the endothelium, but the magnetic action is not sufficient to crush the porous sclera to the degree that fluid is precluded from flowing therethrough into the corneal stroma.

SUMMARY OF THE INVENTION

A general object of my invention is to provide apparatus that will assist in the preservation of a cornea until it is needed for transplanting. In this regard, an aim of the invention is to avoid contact or physical engagement with the endothelium of the cornea, and at the same time uniformly compress the sclera to a degree that fluid will not enter the corneal stroma through the porous structure of the sclera.

While the above object effectively avoids any deleterious contact between any part of my apparatus and the endothelium, my invention has for a correlated object the avoidance of any mechanical or human contact with the endothelium while the clamped cornea is being handled or moved about prior to and after storage. Another object of the invention is to provide apparatus that not only effects a firm clamping action without damage to the cornea but which apparatus is of simple construction and which can be inexpensively manufactured.

Yet another object of the invention is to provide apparatus that effectively holds a cornea which can be readily and quickly manipulated so as to both clamp and later release the cornea therefrom without difficulty.

Briefly, my invention envisages a base ring member having a flat bottom and a frusto-conical portion having an upper surface over which the sclera of the cornea is placed, the frusto-conical portion having a central opening of a size such that the periphery of said opening will reside beneath an annular portion of the sclera but outwardly of the cornea. An upper ring member has an opening therein of the same size as the opening in the lower ring member, the two openings being registrable with each other so that the cornea, which is semispherical, can extend upwardly into the upper ring member without being contacted or engaged by any portion of the upper ring member, as well as any portion of the lower ring member. Recapitulating, the edge of the lower opening and the edge of the upper opening, when the two ring members are brought together, engage the sclera at a location sufficiently outwardly of the cornea so as to not cause any damage thereto. Yet the sclera can be sufficiently compressed so that fluid will not pass therethrough into the corneal stroma. Threaded members are pivotally connected to the lower ring member and by means of wing nuts on the threaded members the upper ring member can be axially forced in the direction of the lower ring member so as to exert a sufficient amount of pressure against the sclera to literally close off and block the pores thereof that would otherwise provide a path for the flow of fluid therethrough.

BRIEF DESCRIPTION OF THE DRAWING

FIG. 1 is an exploded perspective view exemplifying my apparatus;

FIG. 2 is a top plan view of my apparatus with a cornea being held therein, and

FIG. 3 is a sectional view taken in the direction of line 3—3 of FIG. 2.

DESCRIPTION OF THE PREFERRED EMBODIMENT

The apparatus exemplifying my invention has been indicated generally by the reference numeral 10. Basically, the apparatus 10 comprises two plate members 12 and 14.

Describing the lower plate member 12, it will be observed that it is in the form of a circular ring having an annular flat ledge 16. Extending inwardly and upwardly from the relatively flat ledge 16 is a frusto-conical portion 18. The frusto-conical portion is formed with a central opening 20 extending downwardly therethrough, thereby forming a relatively sharp or line-like edge labeled 22. The underside of the ring 12 has been indicated by the reference numeral 24 and from FIG. 3 it will be perceived that the bottom surface 24 is flat or planar so that it can be readily placed on a table or counter top (not shown).

Extending radially from the ring 12 are quadrantly spaced pairs of ears 26, each pair of ears 26 constituting a clevis. A pivot pin 28 extends through each clevis or pair of ears 26 and also through one end of a threaded element or stud 30. The pin 28 in each instance pivotally mounts the threaded stud 30 so that it can be individually swung through virtually 180°. When the ring 12 is placed on a table or counter top, then the various threaded elements or studs 30 can simply be permitted to extend substantially horizontally and rest against the table or counter top so as not to interfere with the placement of a cornea thereon.

Referring now to the upper plate member or ring 14, it will be observed that it has a lower flat or planar face or surface 32. In this instance, there is a circular opening 34 of the same diameter as the opening 20 in the lower ring 12, thereby forming a second line-like edge 36.

As with the lower ring 12, the upper ring 14 is provided with radially-projecting ears 38 which form clevises for the accommodation of the upper portions of the threaded studs 30 therein. Thus, when the lower ring 12 is placed on a table or counter top, the upper ring 14 can be placed on the lower ring 12 and the studs 30 pivoted upwardly into position between the radially-projecting ears 38.

Downward force can be applied to the upper ring 14 through the agency of wing nuts 40. Inasmuch as there are four angularly spaced threaded elements 30 and four wing nuts 40, it follows that substantial uniform pressure can be exerted in an axial direction downwardly. Both of the rings 12 and 14 are sufficiently rigid so as to resist any flexing thereof during the clamping action which takes place when the wing nuts 40 are twisted or tightened sufficiently to cause their undersides to bear against the upper edges of the ears 38 belonging to the upper ring 14.

In order to picture with greater clarity the apparatus 10, FIG. 1 omits the cornea 50 and its integral sclera 52 appearing in FIGS. 2 and 3. Although medical personnel familar with ophthamology will understand the structure of the cornea 50, as well as the sclera 52 attached thereto, it should perhaps be explained that the central cornea or button is usually considered to be comprised of five layers: (1) epithelium, (2) Bowman's membrane, (3) stroma, (4) Descemet's membrane, and (5) endothelium. The foregoing layers have been listed in an anterior to posterior order. Owing to the delicate nature of the endothelium, which lines the posterior surface of Descemet's membrane, it becomes extremely important that this layer remain untouched; otherwise it will die and its deturgescence function; which is needed to maintain normal corneal thickness, destroyed. While the endothelium constitutes an outer layer of the cornea 50, the stroma constitutes an intermediate layer.

The stroma merges into a peripheral layer of tissue called the sclera and which has been labeled 52. Because the sclera 52 is formed of fibrous tissue intermixed with fine elastic fibers with interconnected cell spaces or voids between the fibers, it follows that the sclera 52 is sufficiently porous to enable the passage of fluids, the fluids readily entering via its peripheral edge and flowing unobstructively to the cornea 50 if not prevented from doing so. My invention precludes such a flow of any liquid.

Therefore, in order to afford all of the protection that is demanded of a cornea, such as the cornea 50, it is important that the rings 12 and 14 be properly dimensioned. In this regard, it should be understood that the openings 20 and 34 have a diameter on the order of 12 millimeters, such a dimension being sufficiently great so as to avoid any contact or engagement with the cornea 50 when held by my apparatus 10, as illustrated in FIGS. 2 and 3. While it is important that the diameters of the openings 20 and 34 be sufficiently great so as to not cause any engagement of the two rings 12 and 14 against the cornea 50, the diameters should be sufficiently small so that the edges 22 and 36 bear against only the sclera 52. In order to adequately support the sclera 52, which has a natural annular inclination imparted thereto, as will be discerned in FIG. 3, the frusto-conical configuration of the portion 18 enables the cornea 50 to be supported with the same degree of concavity as is natural. Hence, the dimensions of the lower ring 12, that is the surface providing the frusto-conical portion 18, extends radially outwardly and downwardly to such a degree that the complete support of the sclera 52 is furnished. In this regard, it is planned that the surface of the frusto-conical portion 18 be on the order of seven millimeters in width. This is measured from the edge 22 of the opening 20 to the inner edge of the annular ledge 16.

The rings 12 and 14 are preferably made of stainless steel. Their thicknesses should be sufficient to resist any flexing. In practice, the ring 12 at its periphery should have a thickness on the order of 3.5 millimeters and a central thickness of at least twice this dimension, preferably three times as thick when measured from the edge 22 downwardly to the bottom surface 24. The upper ring 14, it has been determined, should possess a thickness of approximately five millimeters.

Thus, when the wing nuts 40 are tightened, the upper ring 14 is drawn axially downwardly in the direction of the lower ring 12 so as to apply uniform pressure through 360° against the sclera 52. The sclera 52, in this way, can be completely crushed so as to prevent any flow of fluid therethrough. As already mentioned the sclera 52 has a natural porous tissue structure which permits the flow of fluid therethrough if not prevented. It should be borne in mind that the endothelium acts as a pump that pumps fluid out of the corneal stroma to keep the cornea thin. However, when the fluid can enter back into the stroma via the sclera 52, augmented by the preserving media, it follows that the stroma 52 cannot be maintained thin as is necessary if the cornea 50 is to be adequately evaluated as donor tissue for future keratoplasty.

It should be recognized that the underlying side 24 of the ring 12, being flat or planar, forms an acute angle with the flat underside 32 of the ring 14, such angle being indicated by the numeral 54. This leaves an outwardly diverging or flared void for the accommodation of the uncompressed or outward portion of the sclera 52. It is only a radially thin annular portion. This tourniquet-like action effectively precludes fluid flow into the cornea stroma, doing so without any injury to the endothelium constituting the lower side of the cornea 50 as viewed in FIG. 3 of the sclera 52 that is compressed, this being so by reason of the edges 22 and 36 pressurally acting against the lower and upper surfaces, respectively, of the sclera 52.

I claim:

1. Apparatus for aiding in the storing and preserving of a human cornea to be subsequently transplanted comprising a first relatively rigid plate member having a raised central section providing a first surface formed with a first circular opening therein having a diameter on the order of 12 millimeters to provide one relatively sharp, line-like edge for bearing against only the sclera of the cornea to be preserved, said first surface sloping downwardly from said one relatively sharp, line-like edge at an angle to a location spaced sufficiently from said one edge so as to underlie and support all of the sclera integral with the human cornea to be preserved, said angle corresponding to that forming the natural concavity of the sclera of the human cornea so as to provide said support, a second relatively rigid plate member providing a second surface formed with a second circular opening therein to provide a second relatively sharp, line-like edge registrable with, and of a size also on the order of 12 millimeters so as to be engageable with said one relatively sharp, line-like edge of the first circular opening in the absence of a cornea, said first and second surfaces diverging outwardly from the edges of said relatively sharp, line-like first and second openings, and spaced respective clamping means acting in a direction to pull said members toward each other, said openings adapted to accommodate therein the cornea to be preserved free of engagement by said first and second members in that only the relatively sharp, line-like edges of said first and second openings bear against the sclera integral with the cornea to be preserved.

2. Apparatus in accordance with claim 1 in which said raised central section constitutes a frustoconical portion corresponding to the natural cavity of the sclera of the human cornea, said frusto-conical portion having said first circular opening extending therethrough.

3. Apparatus in accordance with claim 2 in which one side of said second member is flat so that an outwardly flaring void is provided when said members are in a confronting relationship with each other, said void freely accommodating that portion of the sclera extending beyond said circular openings, said first surface having a width on the order of 7 millimeters.

4. Apparatus in accordance with claim 3 in which said plate members constitute first and second rings, each ring having outwardly projecting spaced pairs of radially directed ears, said clamping means including a threaded element pivotally connected at one end between each pair of ears of said first ring and having its other end receivable between an associated pair of said ears on said second ring, and a wing nut threadedly received on each threaded element for causing said rings to be pulled toward each other, thereby clamping the sclera belonging to the cornea to be preserved between the portions of said first and second rings circumjacent their said openings.

5. Apparatus for aiding in the storing and preserving of a human cornea to be subsequently transplanted comprising an upper and a lower relatively rigid cooperable ring member for compressively engaging only the sclera therebetween which is integral with the cornea to be preserved, said ring members each having a central opening extending therethrough for freely encircling and accommodating the cornea, said openings having diameters on the order of 12 millimeters to provide the same cross section forming registrable and matable relatively sharp, line-like edges for compressively engaging said sclera, said lower ring member having a first surface sloping downwardly and outwardly from the relatively sharp, line-like edge of its opening in a direction away from its said opening and said upper ring member having a generally flat surface extending horizontally and outwardly from the relatively sharp, line-like edge of its said opening, said first and second surfaces forming an acute angle with each other and said first surface extends to a location spaced sufficiently from the opening of said lower ring member so as to underlie and support all of the sclera integral with the cornea to be preserved, the angle of said first surface corresponding to that forming the natural concavity of the sclera of the human cornea to provide said support, and respective means interengaging said ring members at angularly spaced locations for urging said upper ring member axially in the direction of said lower ring member to compress the sclera between said relatively sharp, line-like edges to prevent fluid flow from the outer peripheral edge of the sclera into the cornea.

6. Apparatus in accordance with claim 5 in which said interengaging means includes a plurality of quadrantly spaced threaded elements, a plurality of radially projecting clevises on said first ring member equal in number of the number of threaded elements, one end of each threaded element being pivotally secured to one of said clevises, and a plurality of radially projecting clevises on said second ring member, the other ends of said threaded elements being receivable in said last-mentioned clevises, and a threaded nut member on each of said other ends for urging said first ring member axially in the direction of said second ring member to compress said sclera between said relatively sharp, line-like edges, the degree of tightening of said nut members determinng the extent said sclera is compressed and hence the degree the flow of fluid through the sclera into the cornea is prevented.

7. Apparatus in accordance with claim 5 in which said first surface has a width on the order of 7 millimeters.

8. Apparatus in accordance with claim 5 in which said first member includes an annular flat edge, said first surface sloping at the same angle throughout its width to said annular flat edge.

9. A method for aiding in the storing and preserving of a cornea to be subsequently transplated comprising the steps of first placing the sclera of the cornea to be stored on a first relatively rigid plate member having a raised central section providing a first sloping surface formed with a circular opening therein to provide one edge of a size so that the sclera engages both said central section and said one edge, and so that the cornea is located in a spaced relation from said one edge, placing a second relatively rigid plate member providing a second surface formed with a second circular opening therein to provide a second edge that is registrable with said one edge so that said sclera resides between said edges, said first and second surfaces diverging outwardly from the edges of said first and second openings when said second plate member has been positioned on the upper side of said sclera to cause the underside of said sclera to bear against said first edge, and clamping said members in a direction to pull said members toward each other so that the edges of said first and second openings are forced only against the sclera and not the cornea to compress said sclera sufficiently so that fluid will not flow therethrough.

10. A method of aiding in the storing and preserving of a cornea to be subsequently transplanted comprising the steps of positioning the sclera of the cornea to be transplanted over a generally frusto-conical portion of a member having a central opening therein, the opening therein being sufficiently large so as to not engage any portion of the cornea, placing a ring member having an opening corresponding generally in size with the opening in said frusto-conical portion in registry with the opening in said frusto-conical portion with a circular portion of the sclera therebetween, and then pressing said upper ring member in a direction toward said frusto-conical portion so as to compress the ring section of said sclera only to such a degree as to effectively close off and block the pores of said sclera to thereby prevent a path for the flow of fluid through said sclera.

* * * * *